United States Patent [19]

Chou

[11] Patent Number: 4,701,406

[45] Date of Patent: Oct. 20, 1987

[54] ASSAY FOR THE DETECTION OF EPIGENETIC TOXIC (NON-GENOTOXIC) SUBSTANCES

[75] Inventor: Iih-Nan Chou, Newton, Mass.

[73] Assignee: Trustees of Boston University, Boston, Mass.

[21] Appl. No.: 685,828

[22] Filed: Nov. 16, 1984

[30] Foreign Application Priority Data

Nov. 16, 1984 [WO] PCT Int'l Appl. .................. PCT/US84/01877

[51] Int. Cl.$^4$ .................... G01N 33/50; G01N 33/53; G01N 33/567; G01N 33/574
[52] U.S. Cl. .......................................... 435/7; 424/3; 435/29; 436/63; 436/64; 436/519; 436/813
[58] Field of Search ...................... 424/3, 309; 435/29, 435/7; 436/63, 64, 519, 813

[56] References Cited

U.S. PATENT DOCUMENTS 4,404,181  9/1983  Mauthner .............................. 424/3

OTHER PUBLICATIONS

Parness, J. et al., Biochem. Biophys. Res. Commun., 105(3), 1082–1089 (1982).
Chemical Abstracts, I, 93: 160973t (1980).
Chemical Abstracts, II, 95: 72889f (1981).
"Cellular Systems for Toxicity Testing", G. M. Williams et al., eds., Annals of the New York Academy of Sciences, vol. 407, New York, 1983.

*Primary Examiner*—Sidney Marantz
*Attorney, Agent, or Firm*—David Prashker

[57] ABSTRACT

An in vitro assay procedure for the detection of non-genotoxic substances is provided which utilizes a prepared cell culture whose cytoskeleton constituents are structurally identifiable as microtubules, intermediate filaments and microfilaments. The procedure combines the test sample with the cultured cells and detects a presence of epigenetic substances by identifying structural changes in the cytoskeletal constituents in comparison to normal control cells. The assay method is rapid, accurate, reproducible, and has been demonstrated to identify toxic substances which have not been previously detected by presently known bacterial and/or mammalian cell mutagenic assay systems.

13 Claims, 16 Drawing Figures

ASSAY FOR THE DETECTION OF EPIGENETIC TOXIC (NON-GENOTOXIC) SUBSTANCES

TECHNICAL FIELD OF THE INVENTION

The present invention is directed to the identification of toxic substances and is specifically concerned with in vitro assay methods for the detection of hazardous substances prior to their introduction into industrial and residential environments in order to reduce the risks of human exposure to potential health hazards.

BACKGROUND OF THE INVENTION

One of the major dangers of living and working in a highly complex and technologically advanced society is that we are exposed to a sea of hazardous or toxic substances that have contaminated our living and working environments, the overwhelming majority of which are man-made and often carcinogenic. According to a recent estimate, there are presently over 70,000 chemicals now in commercial production and another 700-3,000 new chemicals are being introduced every year. Among this vast number of industrial chemicals, only approximately 10% have been tested for toxicity, usually in the form of carcinogenicity, in life-time animal studies—in many cases only after extensive or prolonged human exposure. These statistics do not include the profound changes now occuring as a result of exposure to pollutants in water and air which have secondary or tertiary effects upon the bioatmosphere and the natural biological cycles whose importance we are only now recognizing. With so many untested industrial chemical compounds and chemical changes constantly occuring, it has become logistically impossible to test even a significant portion of them for toxicity (in the form of carcinogenicity) by classical toxicological protocols using animals primarily because there is a lack of manpower, insufficient facilities, and inadequate time and financial resources available to undertake this task on such a mammoth scale. This has led directly to the development of in vitro assay methods which are short-term test systems and involve a minimum of manpower and supplies.

A fundamental problem, which has developed as our knowledge has advanced and the variety of test methodologies and systems has expanded and multiplied, has been a lack of precision and consistency in terminology. In view of the unfortunate tendency to use one term for a variety of meanings or applications and in view of the creation of novel terms which are not precisely defined or understood, the following definitions and terms are provided which will aid to clarify and particularly point out major differences and distinctions.

Toxicity and cytotoxicity: specifically induced cellular injury, usually chemically, which occurs in a sequence of phases which may be almost instantaneous or occur as a progressive series over time. The severity of the injury in the cell may be so extreme that the cells are killed almost instantaneously; alternately, the injury will be more subtle, time consuming and be observed as a series of degenerative changes prior to cell death. For all substances other than very rapidly acting agents, the events are considered as occuring in two phases; the early reversible changes and the late irreversible cell changes ending in cell death. Note in particular that carcinogenicity does not necessarily correlate with toxicity; in fact, there are many cytotoxic non-carcinogens and noncytotoxic carcinogens. Toxicity, by definition therfore, includes within it the terms "carcinogenic" and "degenerative".

Carcinogens (or carcinogenic agents): substances for which there is conclusive evidence from human studies which indicates there is a direct causal relationship between exposure to the substance and human cancer. These are to be distinguished from substances which may be "reasonably anticipated to be carcinogens" which are defined and distinguished as those for which there is only limited evidence of a direct causal relationship between exposure and human cancer or sufficient evidence of such a causal relationship in experimental animals. The term is thus limited to situations where cancer or tumor cells (and sarcomas) arise in humans and other animals after exposure without reference to an action mechanism and thus is a functional, operational definition limited to cellular alteration which results in an observable loss of control of normal cell growth leading to unrestrained proliferation and the formation of tumor.

Degenerative substances: compounds inducing cell injury which does not result in the formation of a tumor or cancer cell as such. The degeneration of the intact cell may in fact be reversible after the initial injury; such reversible changes occur early in time and include mild cytoplasmic edema, dilation of the endoplasmic reticulum, slight mitochondrial swelling, disaggregation of polysomes and the occurrence of small aggregates of chromatin around the nucleus. The irreversible changes occur late in the sequence of progressive steps and include expensive mitochondrial swelling with cristae disruption, gross cytoplasmic swelling with dissolution of organelles, plasma membrane rupture, and nuclear dissolution. In vivo clinical/diagnostic observation and examination of human and animal subjects who have been exposed to degenerative substances typically exhibit emphysema, kidney and liver dysfunction, abnormal neurological function, "wasting syndrome"—a loss of body weight and appetite, and other debilatating states The degenerative effects will vary in severity with the dose of exposure in concentrated or dilute form, whether short or prolonged in duration, and in nature with the wide variety of cellular destruction and target areas within the cell which can eventually lead to cell death. This term, therefore, is an operational, functional definition used to identify all types of cell injury regardless of target area or action mechanism which do not give rise to tumor cells as such.

Genotoxicity (and genotoxic substances): a mechanism of induced cell injury which is limited to direct alterations and modifications of the genetic material in the cell exclusively and include DNA damage, gene mutation, and chromosonal effects in both microorganisms (bacteria and fungi) and mammalian cell systems. The mutations are detected as phenotypic changes and can result from alterations in the structure of DNA as base substitutions, frame shifts, large deletions, insertions, and translocations. The DNA damage is measured either by strand breakage or fragmentation or is measured indirectly as consequent DNA excision and repair. The chromosomal effects include multilocus chromosome deletions and non-disjunction as well as chromosomal aberrations such as breaks, terminal and interstitial deletions, rings, translocations, and dicentrics. A common effect of such modifications of genetic material within mammalian cells is the morphological transformation of the normal cell as altered colonies or foci in a monolayer of cells generally characterized by the piling up of the cells in an irregular, criss-cross pattern representing a loss of growth inhibition in cell-to-cell orientation.

Epigeneticity (and epigenetic substances): a mechanism of induced cellular injury which does not involve direct modifications of genetic material. The effected cells may be destroyed progressively over time or be killed almost instantaneously. The epigenetic substance may cause the cell to become a tumor cell and thus be a "carcinogenic" agent or cause progressively debilitating effects in the cell and thus be termed a "degenerative" substance. The term is therefore an operational and functional definition which identifies an action mechanism by which those substances and agents which are non-genotoxic injure the cell in non-genetic pathways.

Tumor initiator: A chemical compound capable of initiating or inducing cell change and injury in normal cells and rendering them into a premalignant state. Although tumor initiators are generally genotoxic agents, this term definitionally is not restricted to this action mechanism.

Tumor promoter: A substance capable of increasing the incidence of tumor formation in vivo when it is applied repeatedly to an animal after it has previously received an appropriate dose of a tumor initiator. A tumor promoter by itself cannot induce tumor formation nor can it initiate alterations in normal cells which result in the formation of premalignant cells. This term (and its counterpart, "tumor initiators") are also applicable to cultured cells which have been morphologically transformed in vitro into tumor or malignant cells. This term, by definition, does not make any indication or reference to the precise nature or action mechanism of cell injury leading to the transformation. In contrast, substances or agents which act as both initiators and promoters themselves are said to be "carcinogenic" and are not the equivalent of either a "tumor initiator" or a "tumor promoter" as such.

Cytoskeleton pertubation: The disruption or disorganization of specific cytoplasmic filamentous elements or components within the cell without reference to or specification of a mechanism of cellular alteration. The disruptions comprise the disassembly or the depolymerization of microtubules, intermediate filaments and microfilaments, elements which collectively identify and form the complex network of organized filamentous structures within the cell proper. The distribution and organization of these elements in the cytoplasm, although varying from cell type to cell type, is substantively involved in regulating the cellular morphology and shape, motility, mobility of surface receptors, and internal organization of the cell. Any significant change in the structure or organization of these cytoskeleton elements results in a microscopically visible manifestation of cellular injury within the cell.

The technical advances leading to the development of short-term test systems for the detection of toxic or hazardous substances, particularly carcinogenic agents, has grown enormously in recent years. Much detailed information regarding toxicity testing using bacterial and mammalian cell assays and their limitations is found in the following publications: *Cellular Systems For Toxicity Testing* (Williams et al, editors)Annals Of The New York Academy Of Sciences, Volume 407, 1983; *Third Annual Report On Carcinogens Summary*, September 1983, Public Health Services, U.S. Department of Health and Human Services; *National Toxicology Program, Ad Hoc Panel Draft Report On Chemical Carcinogenesis Testing and Evaluation*, 1984, U.S. Gov't. and National Toxicology Program Annual Plan, 1983. In view of these publications and the many references cited therein, the overall effect and state of test systems for the detection of toxic substances may be summarized as follows. Although long-term animal studies have been traditionally accepted as the only experimental laboratory method suitable for providing conclusive evidence of either toxicity or carcinogencity of a substance, short-term in vitro test methods are available which are more efficient, economic and faster. Although many different systems have been proposed for such testing purposes [reviewed extensively by Hollstein et al., Mutat. Res. 65:133–226 (1979)], only a relative few have been recognized as being accurate and have thus correspondingly received significant widespread use including incorporation into the genetic toxicity testing program under present evaluation by the National Toxicology Program. These include: the Salmonella/Ames assay [Ames et al., *Mutat. Res.* 31:347–364 (1975) and subsequent modifications; the mouse lymphoma systems for point mutations [Amacher et al., *Mutat. Res.* 64:391–406 (1979)]; the CHO system for chromosome aberrations and sister chromatid exchange (SCE) [Evans, *Ann. N.Y. Acad. Sci.* 407:131–142 (1983); Wolff, *Ann. N.Y. Acad. Sci.* 407:142–153 (1983)]; and the Drosophila mutagenesis assay [Rasmuson et al., *Mutat. Res.* 54:33–38 (1978); Vogel et al., in *The Predictive Value of Short Term Screening Tests in Carcinogenecity* (Williams et al.,editors), Elsevier/North Holland Biomedical Press, Amsterdam, The Netherlands, pages 125–147, 1980]. Other tests under present evaluation include assays for unscheduled DNA synthesis, aneuploidy, chromosome aberrations and SCE in vivo, cell transformation, and cell to cell communication (metabolic cooperation) [Williams et al., *Ann. N.Y. Acad. Sci.* 407 (1983); *The Use of Human Cells For The Evaluation of Risks From Physical and Chemical Agents* (Castellani, ed.), Plenum Press, N.Y. 1983; *Chemical Mutagens Principles and Methods For Their Detection* (de Serres and Hollaender, eds.), Volume 8, Plenum Press, N.Y. 1983].

The common feature of all these short-term in vitro assay systems is their reliance and dependence upon genotoxic mechanisms per se. By definition therefore, all these assay methods identify the presence of a toxic substance that directly damages DNA or causes cellular injury by inducing alterations and/or modifications in the genetic material as measured by mutagenesis or chromosomal effects directly or indirectly. This limitation and restriction has been deemed to be both acceptable and reliable because there is a very high correlation between genotoxicity per se (and genotoxic test systems by extension) and carcinogenicity (evidence of cancers in humans or animals clinically identified). Consequently, genotoxicity in several test systems has been taken as presumptive evidence of carcinogenicity [Williams and Weisburger, *Ann. Rev. Pharm. Tox.* 21:393–416 (1981); Weisburger and Williams, *Science* 214:401–407 (1981); Ames and McCann, *Cancer Res.* 41: 4192–4203 (1981); Brusick, *Ann. N.Y. Acad. Sci.* 407:164–176 (1983); Bartsch, *Ann. N.Y. Acad. Sci.* 407:351–361 (1983)]. Comparison of the data revealed in these publications and many others show that certain classes of carcinogens (e.g., polycyclic aromatic hydrocarbons, alkylating agents, nitrosamines, aromatic amines and others) uniformly showed an excellent (90–100%) genotoxicity (mutagenicity)—carcinogenicity correlation. However, other classes of recognized carcinogens, best exemplified by certain metals, steroid hormones and chlorinated hydrocarbons as found in pesticides and tumor promoters consistently showed very poor responses in the Ames and/or mammalian cell genotoxic assay systems. This has led to the recognition that carcinogens in general should be classified operationally as genotoxic and epigenetic agents [Williams, *Ann. N.Y. Acad. Sci.*, 407:328–333 (1983) and the references cited therein]. By this proposal, those substances, particularly carcinogens, which are capable of interacting directly with genetic materials such as DNA are termed genotoxic exclusively and can be identified by mutagenicity tests currently in use; on the other hand, epigenetic substances including not only carcinogens but also tumor promoters and other toxicants, do not induce cellular damage leading to observable genetic alterations or mutations and in fact can be identified only poorly by the presently available short-term tests. Although the need for non-genotoxic short-term reliable tests for the detection of epigenetic substances has now been recognized, no validated in vitro tests for this purpose are yet available. A major gap in all short-term testing programs thus exists in all investigations and studies now employed for the detection of toxic substances generally.

SUMMARY OF THE INVENTION

The present invention is an in vitro assay for the detection of non-genotoxic substances in a test sample which comprises the steps of: preparing a culture of mammalian cells whose cytoskeleton elements are structurally identifiable, these elements being selected from the group consisting of microtubules, intermediate filaments and microfilaments; combining the test sample with the cultured cells as a mixture for a predetermined time period; fixing the cells of this mixture; and detecting an identifiable change in the structure and organization of the cytoskeleton elements within these cells, the structural change in the cytoskeleton elements identifying the presence of an epigenetic toxic substance in the sample. This assay method will identify a variety of epigenetic toxic substances which have been consistently categorized as non-toxic (negatives) in presently known mutagenicity assay systems while concomitantly being recognized as carcinogens, tumor promoters, or degenerative substances in epidemiological studies and human exposure. The assay method is rapid, reproducible, and has precise end point determinations for use as a precise and accurate short-term test.

BRIEF DESCRIPTION OF THE DRAWING

The present invention may be more completely fully understood when taken in conjunction with the accompanying drawing, in which:

FIG. 1 is a series of photographs which illustrate the microscopically visible cytoskeleton elements in cultured cells before and after exposure to known toxic substances.

FIG. 2 is a series of photographs demonstrating the cytoskeletal effects of known toxic substances and taxol, alone and in combination, upon cytoskeleton elements.

DETAILED DESCRIPTION OF THE PREFERRED EMBODIMENT

The present invention is an assay method for the detection of non-genotoxic or epigenetic substances via a shortterm in vitro methodology utilizing mammalian cells in monolayer cultures. The assay system relies upon the identification of cytoskeleton perturbation as the specific means of identifying those substances which manifest cellular injury using a mechanism not involving alteration or modification of the genetic material, directly or indirectly. The cytoskeleton collectively refers to a complex network of cytoplasmic filamentous structures consisting of three major components: microtubules (hereinafter "MT"), intermediate filaments (hereinafter "IF") and microfilaments (hereinafter "MF"). The existence of these cytoskeletal constituents, their distribution, and their organization and function within the cytoplasm of the cell in terms of their role in regulating cellular morphology and shape, motility, mobility of surface receptors, internal organization of the cell, and other functions is well known to cellular and molecular biologists and biochemists [*Cell Motility* (Goldman et al., Editors), Cold Spring Harbor Conferences on Cell Proliferation, Books A,B,C, 1976; *Organization of the Cytoplasm*, Cold Spring Harbor Symposium Quantitative Biology, Vol. 46, Cold Spring Harbor, 1981; Lazarides, *Ann. Rev. Biochem.* 51:219–250 (1982)]. The role of these cytoskeleton elements as intracellular structures for the control and continuity of cytoplasmic organelles and membrane components of the cell surface has been the traditional focus of investigators [Hynes, *Cell Surface Reviews* 7:97–136 (1981); Hynes and Destree, *Cell* 15:875–886 (1978); Heggeness et al.,*Ann. N.Y. Acad. Sci.* 312:414–417 (1978)]. The present assay method utilizes the disruption of these cytoskeleton elements as determined by microscopic observation as the useful and reliable end point in a cellular toxicity assay for the screening of hazardous and/or toxic chemicals and other epigenetic substances.

The preferred mode of carrying out the assay is as follows:

A. Preparation of Cell Cultures

Monolayer cultures of mouse Swiss 3T3 cells are routinely grown in Dulbecco's Modification of Eagle's medium (hereinafter "DME") supplemented with 10% fetal bovine serum (hereinafter "FBS"), penicillin (100 units/ml) and streptomyocin (100 µg/ml), and incubated in a humidified atmosphere with 5% $CO_2$ following procedures known in the art [Schroder et al., *Cancer Research* 40:3080–3094 (1980)]. Quiescent, sparse 3T3 cells are regularly obtained by plating trypsinized cells at a density of $3 \times 10^4$ cells per 35 mm diameter Petri dish each containing one or two coverslips ($12 \times 12$ mm, #1 thickness) in 2.0 ml of DME containing 10% FBS and the antibiotics followed by incubation at 37° C. for 20 hours. This medium is then changed to freshly prepared DME having 0.3% FBS and the antibiotics and the cells are allowed to incubate for three additional days at 37° C. to become serum arrested. This is followed by another change of the latter prepared medium and incubation for another 24 hour period before the cells are used. This preparation method yields serum-arrested 3T3 cells having a characteristic morphology which is profoundly different from that of growing 3T3 cells or quiescent 3T3 cells treated with cytotoxic substances.

Although mouse Swiss 3T3 cells are preferred as the cultured cell type, other types of cultured cells are also useful for the testing of specific kinds of epigenetic agents. Accordingly, normal human foreskin fibroblasts (such as type AG 1522) may be routinely grown in Eagle's medium containing a supplement of non-essential amino acids plus 10% FBS and the requisite antibiotics. Such cells are plated at a concentration of $6 \sim 8 \times 10^4$ per 35 mm dish containing 2.0 ml of the medium and incubated at 37° C. in 10% $CO_2$ for 2-3 days to obtain subconfluent cultures for assay use. Other types of cultured cells may also be used with such modifications and supplemental nutritional requirements as are required for that cell type; the variety includes human embryonic lung fibroblasts (WI-38 cells), MDCK epithelial cells, and other cell types previously used for the investigation of the structure and organization of cytoskeleton components.

B. Addition of Test Sample

The test sample to be evaluated is added directly to the quiescent cells in culture. For ease of assay, it is desirable that the substance under test be dissolved in DME, water, or an appropriate organic solvent carrier so that it may easily combine and react with the cells in the presence of culture medium. If introduced in a solvent carrier form, the substance under test need not be soluble as such, but any appropriate solvent carrier which forms a solution, sol, or other fluid mixture is equally useful. Given that this assay procedure may be used with toxic substances other than chemicals as such, it is only required that the substance to be evaluated be in contact with the quiescent cells in some appropriate manner such that the substance and the intracellular components of the cells may react. When testing hazardous physical agents such as light or radiation energy (e.g. UV light at wave lengths ranging from 200–400 nanometers), it is only necessary that the energy be directed at the cells for the specified, pre-determined time period.

In most instances, the reaction time of the sample under test with the quiescent cells in culture need be only a few hours in duration depending on sample dosage. If desired, the exposure time may be as short as 1 hour or be extended as deemed appropriate; incubation periods of 24 hours and greater are easily applicable at dosages below acute toxic levels. In addition, it may be desirable under certain test requirements for repeated exposures of a single substance in order to determine the cumulative effect of repeated exposures; although this itself is not a requisite part of the assay procedure per se, nothing prevents the user from so modifying the procedure as described herein.

C. Fixation Prior to Microscopic Observation

It is preferred that the cells (after being treated with the test substance) be fixed carefully in order to preserve the cytoskeletal components in their true state and structure so that accurate microscopic examination and evaluation may be made subsequently. Preferably, the cultured cells grown on glass coverslips and prepared as described above are gently washed twice with a solution of phosphate buffered saline (hereinafter "PBS") using a volume of approximately 2.0 ml per dish. The cells are then washed once with a microtubule stabilizing buffer, pH 6.9 which contains 0.1 M Pipe [piperazine-N-N'-bis(2-ethanesulfonic acid)], 1 mM $MgSO_4$, 2 mM EGTA [ethyleneglycol bis(2-aminoethyl ether)tetraacetic acid] and 2 M glycerol (hereinafter "PM2G buffer"). The PM2G buffer should be prepared beforehand, be filtered and then stored at 4° C. until used. This buffer effectively preserves microtubules as well as microfilaments and intermediate filaments within the cell during the multi-step process period after removal of the substance under test. This is important so that no further cytoskeleton disruption will occur during processing. The buffered cells are then fixed by adding PM2G buffer containing 3.7% formaldehyde solution which has been freshly prepared from a 37% formaldehyde stock solution and allowing the cells to stand for 30 minutes at room temperature. This is followed by removal of formaldehyde solution, adding PBS to the cells and incubation for 5 minutes at room temperature. The fixed cells are then treated with a solution of PBS containing 0.1 M glycine, pH 7.4 for 5 minutes to quench the effects of the formaldehyde. The cells are then extracted using 0.3% Nonidet P-40 (hereinafter "NP40") which has been freshly diluted in PBS for 10 minutes. The detergent extracted cytoskeletons are then washed twice with PBS before performing the next step. All manipulations are to be carried out at room temperature with reagent solutions being prewarmed to room temperature before use. The described procedure is a modification of that previously known in the art [Solomon et al., *Cell* 18:431–438 (1979); Duerr et al., *Cell* 24:203–211 (1981)].

Other known methods of fixing the cells prior to identifying the condition of their internal structure are useful. For example, a protocol using glutaraldehyde instead of formaldehyde as a fixative and the use of Triton X-100 as the permeabilizing agent has been described as a multi-step procedure which appears to preserve gross morphology as well as the fine ultrastructure [reviewed by Wang et al., *Methods Enzymology* 85:514–562 (1982)]. Similarly, detergents other than NP40 may be substituted and the concentration of the various reagents and buffers as described herein may be modified without substantially effecting the fixation and extraction of the cells themselves. For these reasons, all modifications of these reagents, the fixatives, and the detergents and all equivalent forms thereof are presumed to be within the scope of the present invention.

D. Identifying the Cytoskeletal Structure Within the Cells

The preferred method of observing and examining the cytoskeletal components within the cell utilizes antibody labeling techniques and fluorescent labels. The technique is a modification of that described in the art [Solomon et al., *Cell* 18:431–438 (1979)]. The fixed cells on coverslips are stained with a primary anti-tubulin, anti-actin or anti-vimentin antibodies for single antibody labeling of MT, MF, or IF respectively. Each of these primary antibodies is prepared according to methods well established in the art, is readily available from commercial sources, and for this reason will not be described here in detail. To visualize two cytoskeletal elements within the same cell, a double labeling technique using a combination of two primary antibody types is used.

The coverslips with attached cells fixed and extracted as described above are placed carefully on moist filter paper (Whatman #5) in a plastic chamber or dish, overlayed with 20 µl of the primary antibody solution (from rabbit sources) and the chamber incubated at 37° C. in a $CO_2$ incubator for 30 minutes. The excess antibody solution is drained off and the cells are washed thoroughly by dipping the coverslips five times in each of five beakers containing 50–100 ml PBS at room temperature. The coverslips are then overlayed with a second antibody (preferably goat anti-rabbit IgG, readily available from commercial sources) which has been previously conjugated to a fluorescent probe such as fluorescein isothiocyanate or rhodamine, using known protocols and then incubated in a 37° C. incubator for 30 additional minutes. The coverslips are again washed thoroughly with PBS as described above and finally washed with double-distilled water to remove any residual PBS. The coverslips containing the antibody stained cells are then mounted on standard glass slides using a drop of Gelvatol as the mounting agent, and allowed to harden overnight at 4° C. Mounting of the coverslips on glass slides can also be accomplished by using well-known reagents other than Gelvatol as identified in Wang et al., *Methods Enzymology* 85:514–562 (1982).

The mounted coverslips are then examined microscopically using a fluorescence microscope (Nikon) preferably equipped with appropriate filters for fluorescein and rhodamine fluorescence as well as an automatic camera system. By switching the filter, one can conveniently visualize different cytoskeletal elements within the same cell without changing the field under observation. Such a microscope allows for photographs to be taken of the fine cytoskeletal structure within the cells and thus permits a record of the visual observation itself as well as a means for comparative evaluation of results at a later time. Photographs are routinely taken using Kodak Tri-X Film (ASA 400) and developed using diafine (Kodak) or any other appropriate reagent by preparing the film to an effective rating of ASA 1600.

The preferred procedure for visualizing the cytoskeletons within the cells utilizes immunofluorescent staining of the cytoskeletal components using appropriately labeled antibodies. Other methods for visualizing the fine ultrastructure of a cell such as electron microscopy are also useful to identify the cytoskeleton elements. The preparative procedures for each method of identification follow those known in the art and include any useful modifications from the basic protocol described therein. Similarly, any other method which accurately identifies the nature, state, and form of the microtubules and other cytoskeletal filaments in the treated cells is similarly appropriate for use as part of the assay. The choice and selection of a specific method of cytoskeletal component visualization and identification are thus left to the user's convenience and experience.

The methodology as described herein is useful for the detection of metal and non-metal toxic substances which have consistently failed to be identified by the Ames assay and/or other short-term genotoxicity tests presently in use. Exemplifying the wide range of toxic substances which may be detected in this manner are those given in Table I below.

TABLE I

| Substances | Health Hazardous Activity | Dosage (Duration) | Cytoskeletal Perturbation | Figure Reference |
|---|---|---|---|---|
| A. Metals | | | | |
| 1. As(III) as NaAsO$_2$ | carcinogen | $2.5 \times 10^{-4}$ M (3.0 hrs) | positive | 1b |
| 2. Cd(II) as CdSO$_4$ | carcinogen promoter | $2.5 \times 10^{-5}$ M (3.0 hrs) | positive | 1c |
| 3. Cr(VI) as K$_2$Cr$_2$O$_7$ | carcinogen, promoter | $1.0 \times 10^{-4}$ M (17.0 hrs) | positive | 1d |
| 4. Ni(II) as NiSO$_4$ | carcinogen promoter | $1.5 \times 10^{-3}$ M (22.0 hrs) | positive | 1e |
| 5. Co(II) as CoSO$_4$ | Carcinogen | $4.0 \times 10^{-4}$ M (17.0 hrs) | positive | 1f |
| B. Non-Metal Compounds | | | | |
| 1. 1-Chloro-2, 4-dinitro- benzene (CDNB) | potent skin sensitizer+ | $5.0 \times 10^{-6}$ M (2.0 hrs) | positive | 1g |
| 2. P—Phenylene- diamine (PPD) | potent skin sensitizer+ | $5.0 \times 10^{-4}$ M (3.5 hrs) | positive | 1h |

+Identified by skin patch test

Figure 1A:
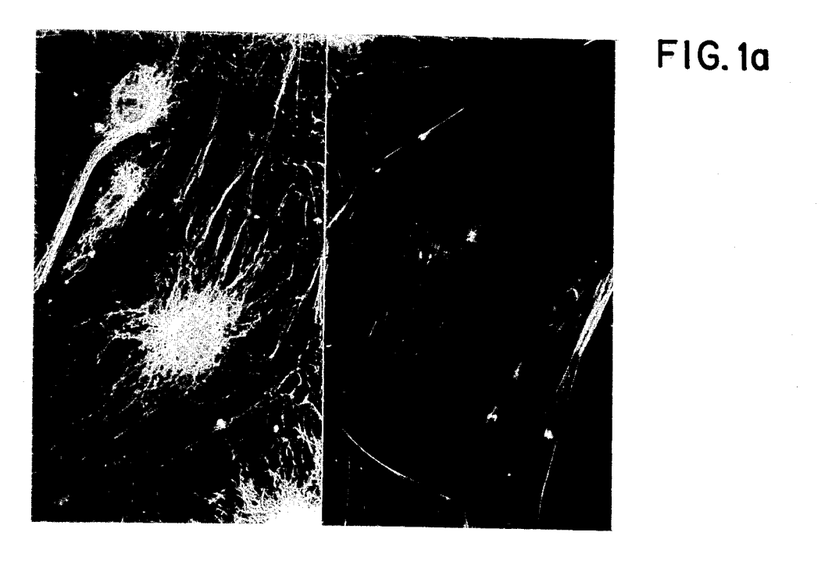
Figure 1B:
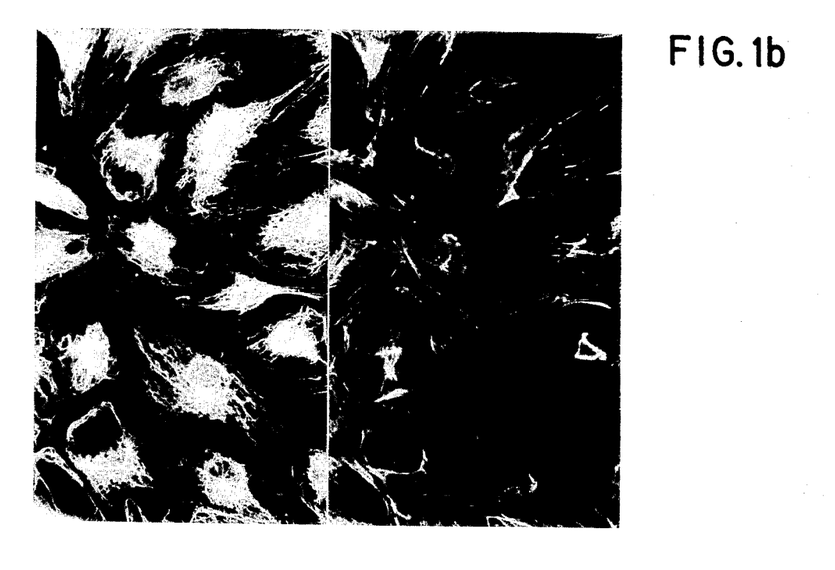
Figure 1C:
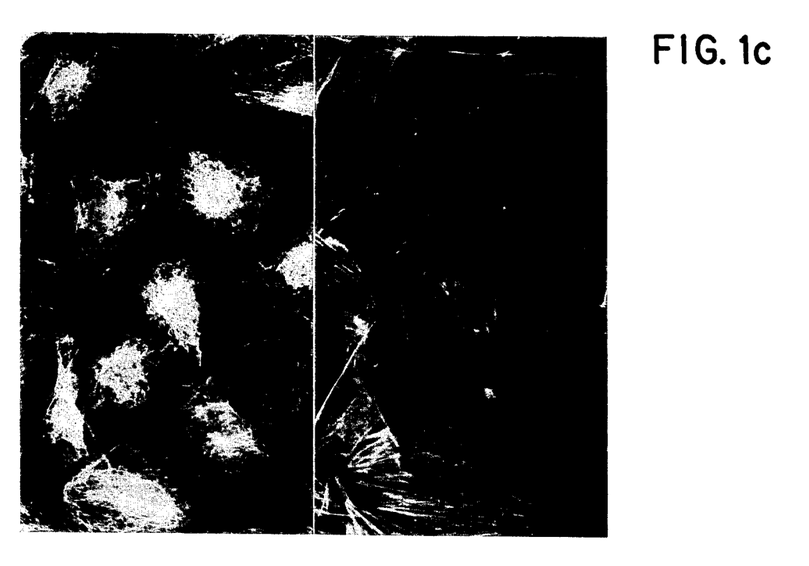
Figure 1D:
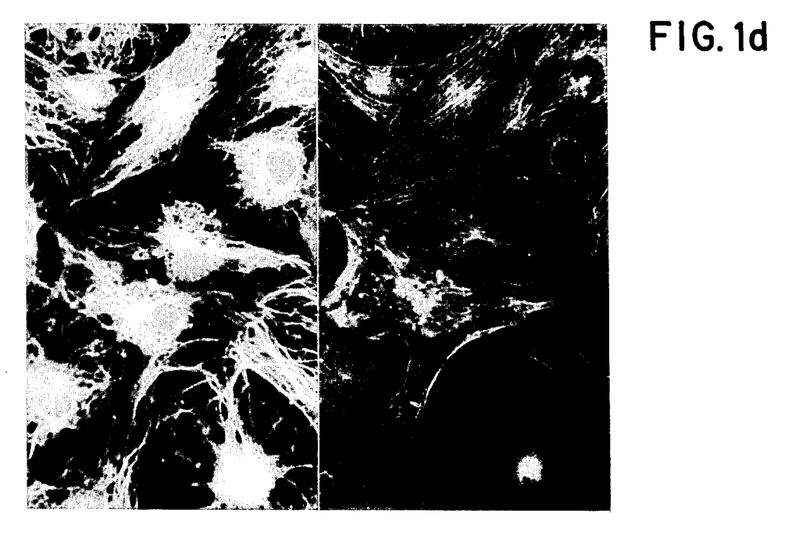
Figure 1E:
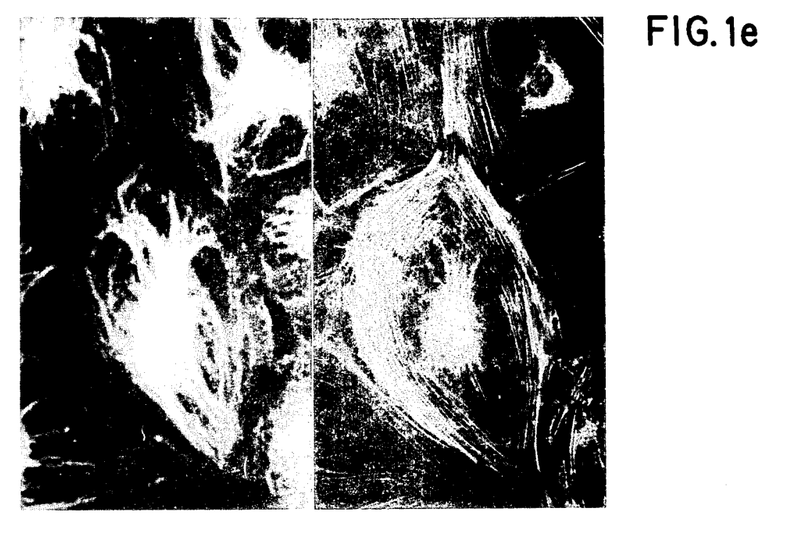
Figure 1F:
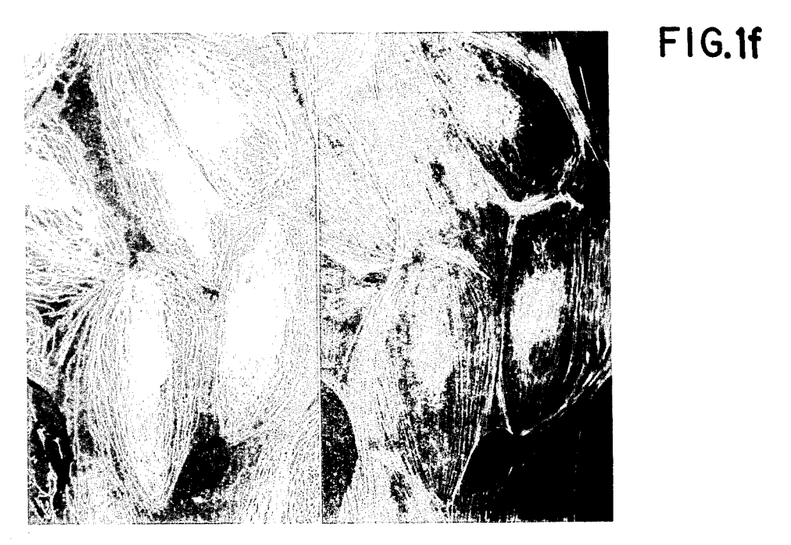
Figure 1G:
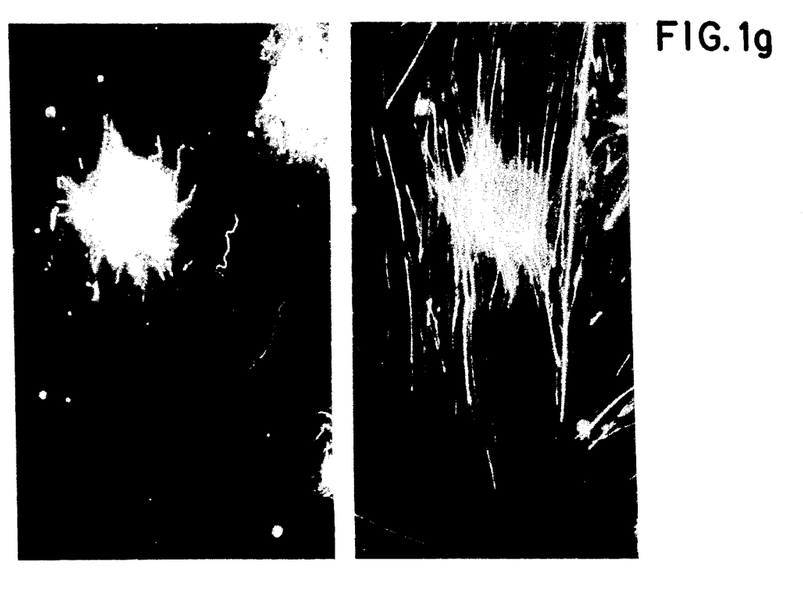
Figure 1H:
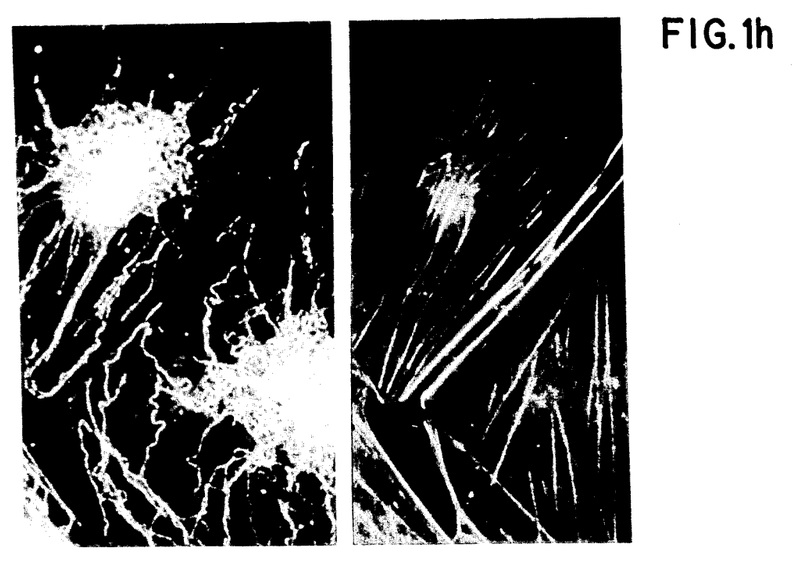
Figure 2A:
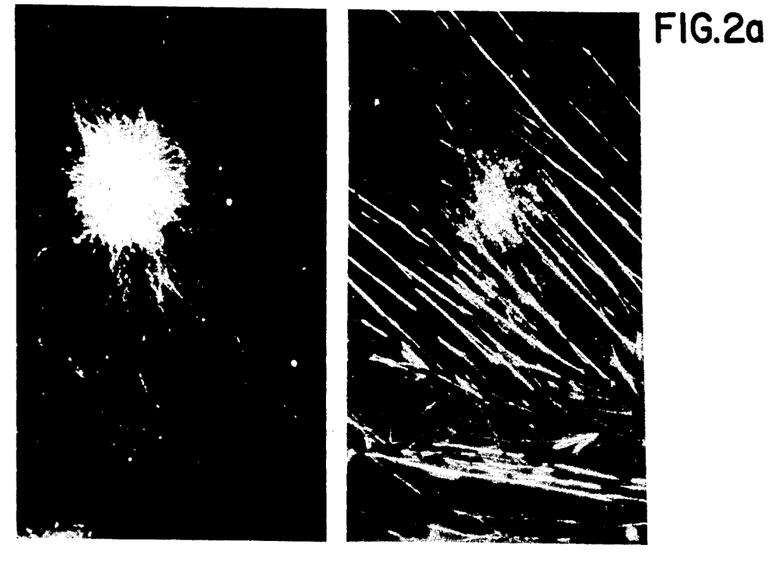
Figure 2B:
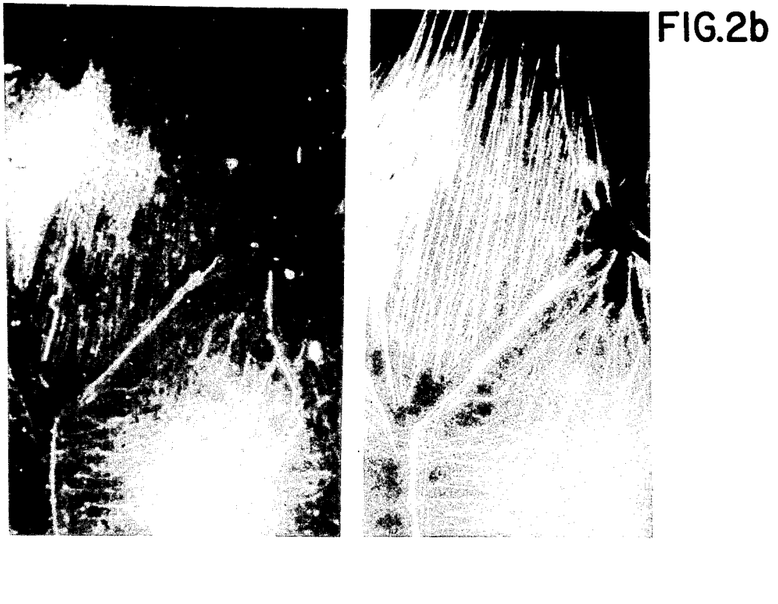
Figure 2C:
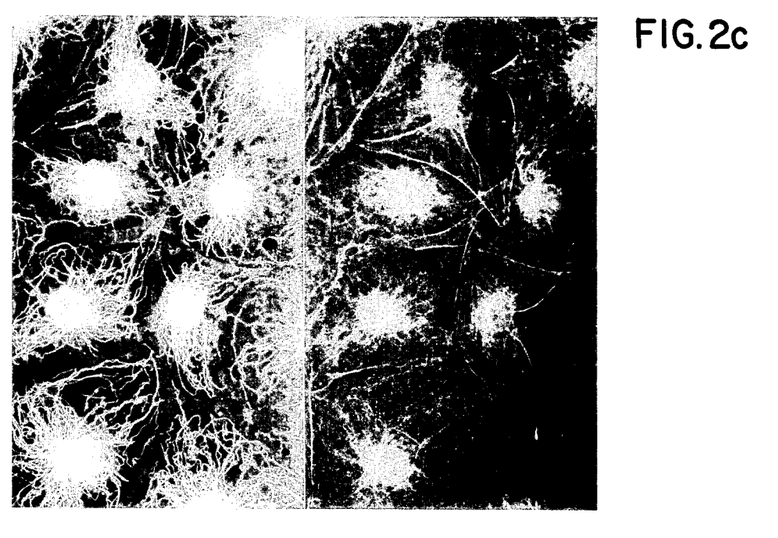
Figure 2D:
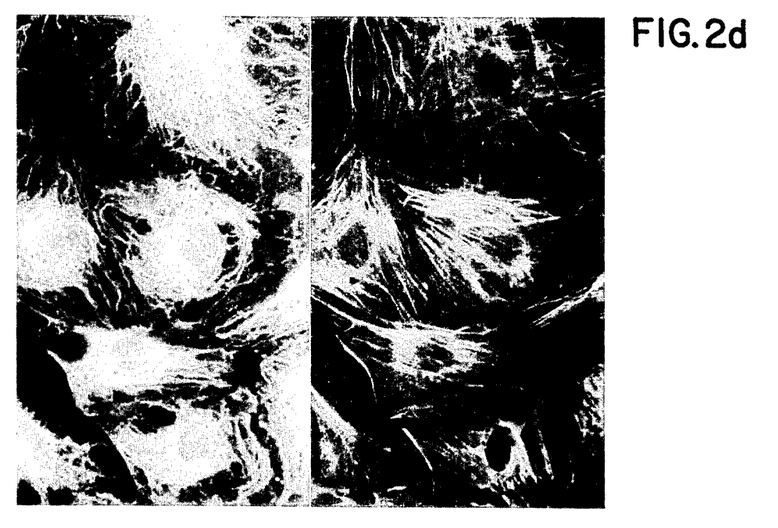
Figure 2E:
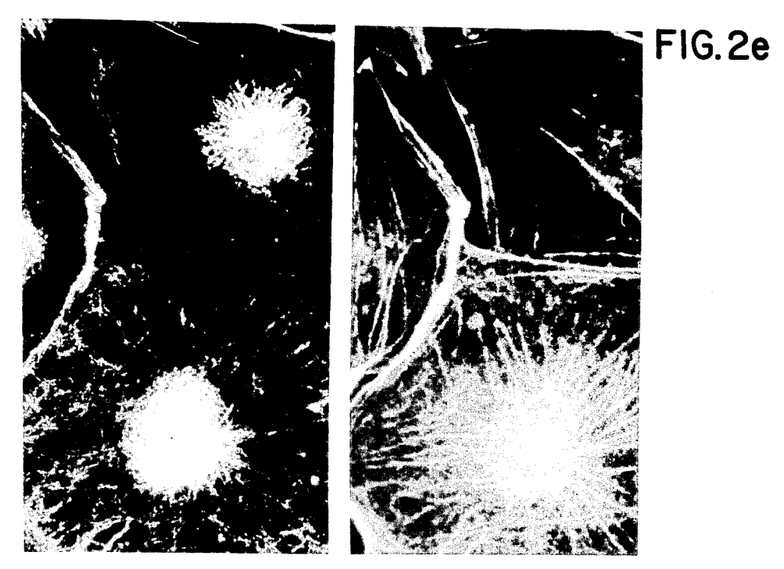
Figure 2F:
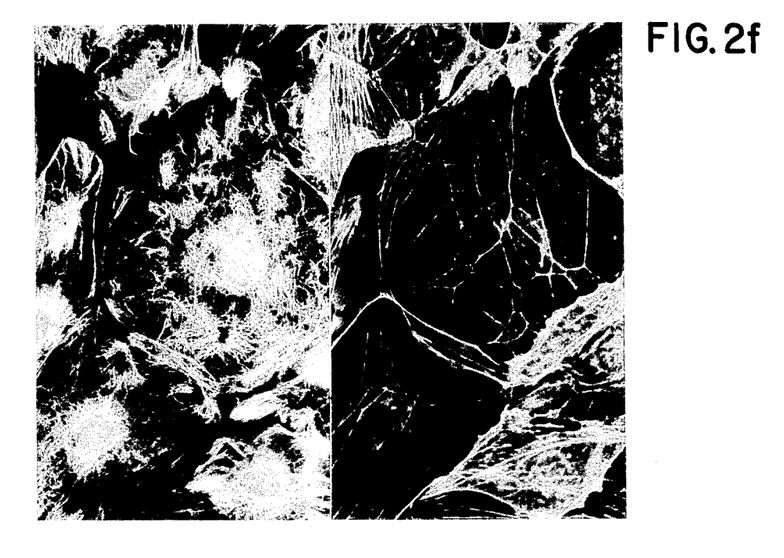
Figure 2G:
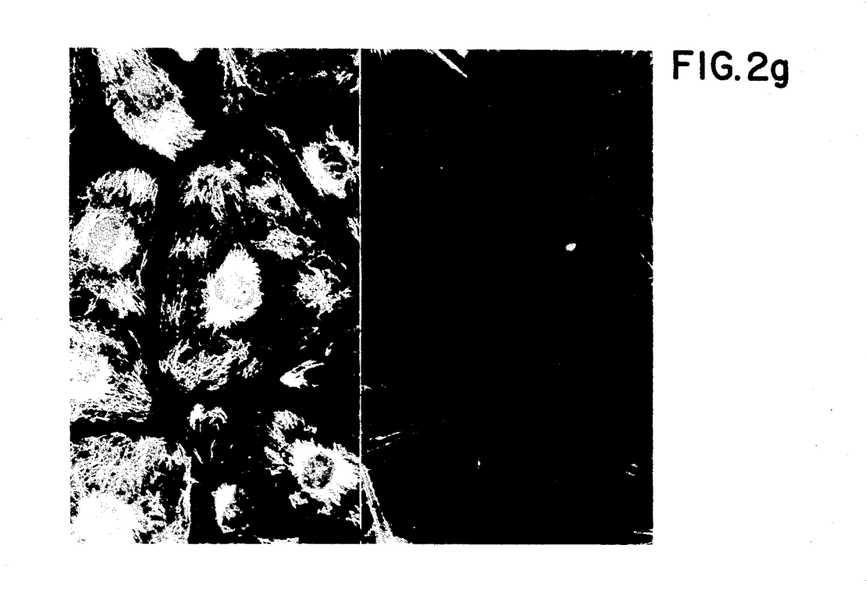
Figure 2H:
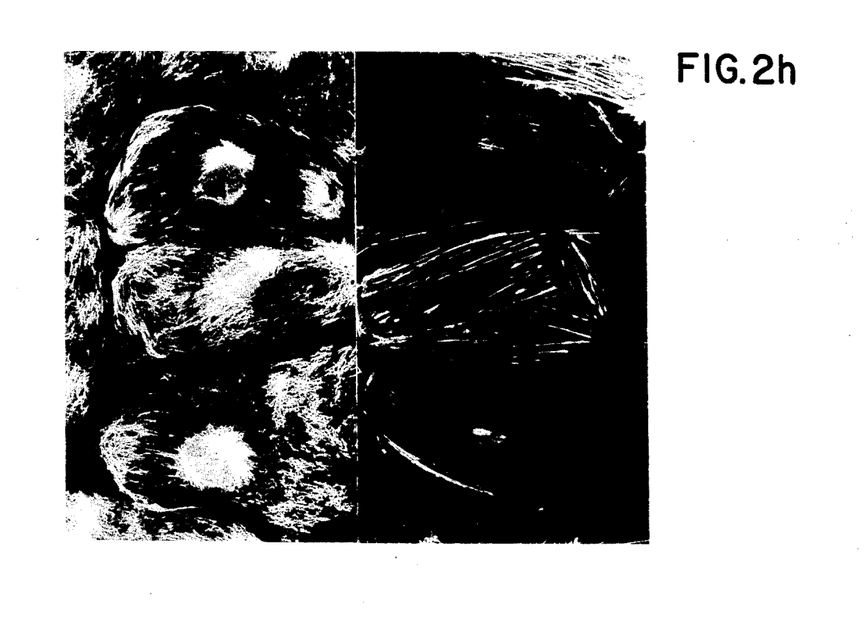

These listed metals are recognized carcinogens, identified as such by the U.S. Department of Health and Human Services, but, with the exception of chromium, have failed to be identified by any of the presently used genotoxicity assays. Similarly, CDNB and PPD are potent skin sensitizers recognized by human as well as animal studies but which also have consistently failed to be identified by the mutagenicity assay mathodologies. Each of these substances is hazardous to human health and is considered as being an epigenetic carcinogen or an epigenetic tumor promoter. The assay results are visually evident as shown by the photographs in FIG. 1. As seen in FIG. 1a, the Swiss 3T3 cells when rendered quiescent by the preparation step described herein and visualized by indirect immunofluorescence microscopy, contain a complex network of microtubules and microfilaments distributed elaborately through the entire cytoplasm. In comparison, treatment of such cells with each of the substances listed in Table I resulted in total or partial disruption of the cytoskeletal elements in a dose and time dependent manner. Furthermore, in some instances, the residual microtubules or fragments thereof remained associated with the star-shaped microtubule organizing center (MTOC) which itself remained attached to the nucleus in most cells (See FIG. 1g). It should be recognized that microscopic visualization of microtubules and microfilaments as seen in FIGS. 1a–1h occurs within the same observable field using different filters and is shown in alternate photographic sequence in each instance.

A variation of the basic assay procedure may also be used to identify not only those substances which are epigenetic toxic agents but also those compounds which are able to inhibit and/or reverse the effects of the toxic substance as well. This is demonstrated by the testing procedure demonstrated in Table II below.

TABLE II

| Substance | Dosage (Duration) | Cytoskeletal Disruption | Figure Reference |
| --- | --- | --- | --- |
| Chlorodinitrobenzene (CDNB) | $5 \times 10^{-6}$ M (2 hours) | positive | 2b |
| Cr(VI) | $1.2 \times 10^{-3}$ M (3 hours) | positive | 2c |
| Ni(II) | $1.5 \times 10^{-3}$ M (3 hours) | positive | 2d |
| CDNB + taxol | $(5 \times 10^{-6}$ M$) +$ $(12 \times 10^{-6}$ M$)$ (2 hours) | negative | 2e |
| Cr + taxol | $(1.2 \times 10^{-3}$ M$) +$ $(12 \times 10^{-6}$ M$)$ (3 hours) | negative | 2f |
| Ni + taxol | $(1.5 \times 10^{-3}$ M$) +$ $(12 \times 10^{-6}$ M$)$ (3 hours) | negative | 2g |
| taxol | $12 \times 10^{-6}$ M (2 hours) | negative | 2h |
| Control Cells | None | negative | 2a |

The visualization of the cytoskeleton protective effects of the antitumor drug, taxol is shown by the series of photographs comprising FIG. 2. Taxol and its analogs and derivatives [Wani et al., *J. Am. Chem. Soc.* 93:23-37 (1971)] is known to promote tubulin polymerization in vitro and microtubule stability [Schiff et al., *Proc. Nat. Acad. Sci. USA* 77: 1561-1565 (1980); Horowitz et al., *Cold Spring Harbor Symposium, Quantitative Biology* 46:219-226 (1982)]. In addition, taxol has been shown to induce in vivo microtubule assembly at multiple sites in the cytoplasm [DeBrabander et al., *Proc. Nat. Acad. Sci. USA* 78:5608-5612 (1981)]. As shown herein, FIG. 2a is a normal cell control; 2b represents the effect of CDNB exposure of cells for two hours. FIGS. 2c and 2d represent 3 hours treatment of quiescent cells to chromium and nickel respectively. FIGS. 2e-2g identify the effects of taxol in combination with CDNB, chromium and nickel given as a single dose. FIG. 2h illustrates the effect of taxol alone on prepared cells in culture. It will be noticed that cells treated with taxol for two hours (FIG. 2h) contain microtubules organized in bundles and have more densely packed microtubule structures than those of control cells (FIG. 2a). However, the presence of taxol in combination with CDNB, chromium, and with nickel not only prevented cytoskeletal disruption but also induced the formation of microtubule bundles into a patchy pattern in individual instances. It is apparent, therefore, that not only are the epigenetic toxic effects of such agents shown by this assay procedure, but also the antagonistic effect of taxol under identical test circumstances is undeniably shown. Furthermore, it has been found that the taxol may be introduced to the cultured cells either prior to or simultaneously with treatment with the epigenetic substances with no discernible difference in effectiveness. Thus, by employing this procedure, not only are epigenetic toxic substances able to be identified, but also those compounds such as taxol and its analogs which are able to counteract and/or antagonize the effects of toxic substances may also be screened and identified effectively.

It is, therefore, believed that the present assay methodology is suitable for the entire range of non-genotoxic substances which are either carcinogenic or degenerative agents; will identify compounds such as tumor promoters which in themselves are not initiators but act synergistically in conjunction with initiating agents to promote tumo and cell transformation in vitro; and can identify compounds, presently known or to be synthesized in the future, which counteract and/or antagonize epigenetic agents.

The range of toxic substances expected to be identifiable using this assay method thus include the following:

(a) Extremely toxic chemicals such as TCDD (2,3,7,8 tetrachlorodibenzo-p-dioxin), steroids and derivatives, metals, and asbestos which are hazardous to human health.

(b) Tumor promoters such as phorbol esters and their derivatives. Many, but not all, tumor promoters have been shown to be inhibitors of metabolic cooperation (intercellular communication). Exemplifying such tumor promoters are phorbol ester derivatives, teleocidin, anthralin, saccharin, oleic and linoleic acids, phenobarbital, butyrated hydroxytoluene, benzoyl peroxide, halogenated aromatic hydrocarbons (such as pesticides) and others (such as indole alkaloids).

(c) Halogenated aromatic hydrocarbons which represent a class of chemicals similar in structure and which produce characteristic patterns of toxic responses. Although individual members of this class vary greatly in potency, they are believed to act by similar mechanisms and uniformly have not been able to be detected or identified except by animal assays or human exposure. These compounds are highly toxic, widespread and persistent environmental pollutants which include: specific congeners of PBB (polybrominated biphenyls) and PCB (polychlorinated biphenyls) and other chlorinated hydrocarbon pesticides such as DDT [trichloro-bis(p-chlorophenyl)ethane], DDE [2,2-bis-(p-chlorophenyl)1,1-dichloroethylene] and dieldrin.

(d) Halogenated (nitro)benzenes and other aryl derivatives which are industrial chemicals present in the environment and recognized as persistent pollutants hazardous to all living systems. Halogenated nitrobenzene derivatives are known to be potent skin-sensitizers, irritants and toxicants. For example, CDNB and FDNB (fluorodinitrobenzene) are powerful skin-sensitizing agents causing severe allergic contact dermatitis. PPD is exemplary of this class of epigenetic toxicants and both CDNB and PPD have been demonstrated as being detectable by the present assay system.

(e) Non-chemical toxic exposure such as the effects of ultraviolet irradiation. Ultraviolet light (hereinafter "UV") comprising light in the range from 200-400 nanometers (nm) has been divided empirically into three types: UV-C comprising the 200-290 nm range which has a demonstrated germicidal effect; UV-B forming the 290-320 nm range which is responsible for sunburn in humans and is now suspected of producing toxic effects; UV-A covering the 320-400 nm range and is believed to induce cytotoxic effect. The cellular effects of UV-A and UV-B radiation are demonstratable using the present methodology. In addition, other physical agents (as opposed to chemical or biochemical substances) will also be detected routinely using the present methodology.

The invention is not to be restricted in form nor limited in scope except by the claims appended hereto.

What I claim is:

1. A detection assay for the detection of a non-genotoxic substance in a test sample comprising the steps of:
   preparing a culture of cells whose cytoskeleton elements are structurally identifiable, said elements being selected from at least one of the group consisting of microtubules, intermediate filaments, and microfilaments;
   combining the test sample with said cultured cells as a mixture;
   fixing said cells of said mixture after a pre-determined time period; and
   detecting an identifiable disruption in the structure and organization of said cytoskeletal elements, said structural and organizational cytoskelton disruption identifying the presence of a toxic substance in the sample.

2. The detection assay as recited in claim 1 wherein said disruption in the structure and organization of said cytoskeletal elements is detected using fluorescent labeled antibodies.

3. The detection assay as recited in claim 1 wherein said cells are fixed by a formaldehyde solution.

4. The detection assay as recited in claim 1 wherein said cells are fixed by a glutaraldehyde solution.

5. The detection assay as recited in claim 1 wherein said fixing of said cells further comprises extraction of the fixed cells with a detergent solution.

6. The detection assay as recited in claim 1 wherein said cultured cells are mouse Swiss 3T3 cells.

7. The detection assay as recited in claim 1 wherein said cultured cells are selected from the group consisting of epithelial cells and fibroblasts.

8. The detection assay as recited in claim 1 wherein said non-genotoxic substance is a carcinogen.

9. The detection assay as recited in claim 1 wherein said non-genotoxic substance is a degenerative substance.

10. The detection assay as recited in claim 1 wherein said non-genotoxic substance is selected from the group consisting of tumor initiators and tumor promoters.

11. The detection assay as recited in claim 1 wherein said non-genotoxic substance is selected from the group consisting of halogenated aromatic hydrocarbons and halogenated benzene derivatives.

12. The detection assay as recited in claim 1 wherein said non-genotoxic substance is an aryl hydrocarbon.

13. The detection assay as recited in claim 1 wherein said non-genotoxic substance is selected from the group consisting of metals, steroids, and asbestos.

* * * * *